United States Patent [19]

Evans et al.

[11] Patent Number: 4,530,838

[45] Date of Patent: Jul. 23, 1985

[54] SYNTHETIC CALCITONIN-GENE-RELATED PEPTIDES FOR LOWERING BLOOD PRESSURE OR GASTRIC ACID SECRETION IN MAMMALS

[75] Inventors: Ronald M. Evans, La Jolla; Larry Swanson, Solana Beach; Wylie W. Vale, Jr., La Jolla; Michael G. Rosenfeld, San Diego; Susan G. Amara, La Jolla; Marvin R. Brown, Del Mar; Jean E. F. Rivier, La Jolla, all of Calif.

[73] Assignee: The Salk Institute for Biological Studies, San Diego, Calif.

[21] Appl. No.: 512,421

[22] Filed: Jul. 8, 1983

[51] Int. Cl.$^3$ .................... A61K 37/02; C07C 103/52
[52] U.S. Cl. .............................. 514/11; 260/122.5 R; 424/95
[58] Field of Search ................ 260/112.5 R, 112.5 T; 424/95, 177

[56] References Cited

PUBLICATIONS

Amara et al., "Alternative RNA Processing . . . ", Nature, vol. 298, 15, Jul. 1982.

Primary Examiner—Donald B. Moyer
Assistant Examiner—Jacqueline M. Stone
Attorney, Agent, or Firm—Fitch, Even, Tabin & Flannery

[57] ABSTRACT

CGRP (calcitonin-gene-related peptide) has the formula:

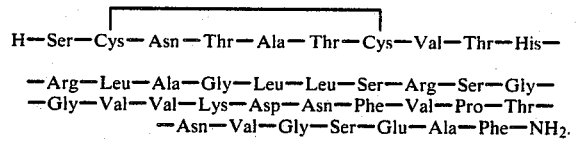

A related peptide has the residue Lys instead of Glu in the 35-position. CGRP or this homolog or pharmaceutically acceptable salts thereof, dispersed in a pharmaceutically acceptable liquid or solid carrier, can be administered to mammals, including humans, to influence memory, mood and pain appreciation and to achieve a substantial lowering of blood pressure or gastric acid secretion over an extended period of time. They also may be administered to affect ingestion behavior, taste and sensory perception.

11 Claims, No Drawings

SYNTHETIC CALCITONIN-GENE-RELATED PEPTIDES FOR LOWERING BLOOD PRESSURE OR GASTRIC ACID SECRETION IN MAMMALS

This invention was made with Government support under Grant Nos. GM-26444 and AM-26741 awarded by the National Institutes of Health. The Government has certain rights in this invention.

SUMMARY OF THE INVENTION

Calcitonin and calcitonin mRNA are found in the thyroid. Analysis of the calcitonin gene and calcitonin gene products by recombinant DNA technologies and direct DNA sequencing allowed the identification of a messenger RNA containing the capacity to encode a 37-residue amidated calcitonin-gene-related peptide, hereinafter termed, CGRP having the formula:

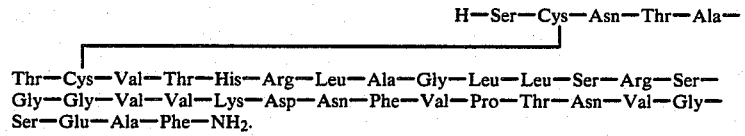

This invention is generally directed to a calcitonin-gene-related peptide (CGRP) and to methods for pharmaceutical treatment of mammals using such a peptide. More specifically, the invention relates to CGRP and a homolog of CGRP, to pharmaceutical compositions containing CGRP or such homolog and to methods of treatment of mammals using CGRP or such homolog.

BACKGROUND OF THE INVENTION

Experimental and clinical observations have supported the concept that neuropeptides play central roles in neurotransmission as well as the regulation of secretory functions of adenohypophysial, pancreatic, adrenalcortical and gut cells. Among the thirty or so neuropeptides that have been implicated in neuronal function in the mammalian central nervous system, several have also been suggested to function as neurotransmitters or neuromodulators primarily in afferant neurons. We have suggested that the application of recombinant DNA technology to the analysis of mRNAs of the brain or other neural tissues may provide a means for identifying new transmitter substances and their related proteins. Thus, following the inferential discovery of novel brain and other neuropeptide transmitters via DNA sequencing technologies, it is possible to synthesize the predicted structure of the new peptide, generate antibody to this peptide and establish the existence, by classical immunohistochemical procedure, of this peptide in various neural tissues. Furthermore, the synthetic peptide itself can be used as a source for identifying and investigating its physiological actions.

Calcitonin is a 32-residue, amidated peptide hormone which was earlier isolated and characterized. Calcitonin is found in both the thyroid and the hypothalamus and has the formula:

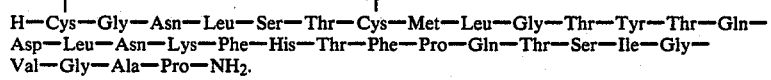

Calcitonin has biological activity in lowering body calcium levels and in promoting absorption of calcium into bone.

Both calcitonin and CGRP are believed to be expressed by the same gene as a result of alternative mRNA processing—sometimes referred to as peptide switching. CGRP mRNA appears to be synthesized in non-thyroid tissue, including brain, spinal cord, adrenals and pancreas. The predicted peptide arising from translation of CGRP mRNA has been identified immunocytochemically throughout the central and peripheral nervous system. CGRP is distributed in brain pathways subserving sensory, motor and autonomic functions. It has also been established that CGRP acts in the central nervous system to stimulate noradrenergic sympathetic outflow.

The synthesis of the 37-residue peptide has been completed and has been found to substantially lower blood pressure for an extended time period. As a result CGRP in substantially pure form (i.e. substantially free of the remainder of a crude biological extract or of related synthetic replicates) should be useful for this and other applications, and CGRP having a purity of about 90% or higher is practically obtainable and can be employed in clinical testing.

An homolog of the 37-residue peptide CGRP having the following formula is considered to have substantially the same biological activity:

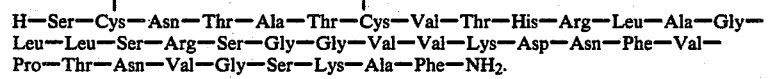

Pharmaceutical compositions in accordance with the invention include CGRP or its homolog, or nontoxic addition salts thereof, dispersed in a pharmaceutically acceptable liquid or solid carrier. Such peptides or pharmaceutically acceptable addition salts thereof may be administered to mammals in accordance with the invention for the lowering of blood pressure, for the regulation of mineral and bone metabolism, the secretion of other hormones and neuropeptides and/or for affecting mood, appetite, behavioral and gastrointestinal functions.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the N-terminal appears to the left and the C-terminal to the right. Where the amino acid residue has isomeric forms, it is the L-form of the amino acid that is represented herein unless otherwise expressly indicated.

The invention provides CGRP and a homolog of CGRP having the following formula (I):

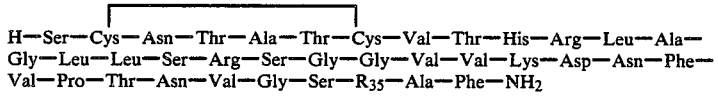

H—Ser—Cys—Asn—Thr—Ala—Thr—Cys—Val—Thr—His—Arg—Leu—Ala—Gly—Leu—Leu—Ser—Arg—Ser—Gly—Gly—Val—Val—Lys—Asp—Asn—Phe—Val—Pro—Thr—Asn—Val—Gly—Ser—$R_{35}$—Ala—Phe—$NH_2$ wherein $R_{35}$ is Glu or Lys. Although not specifically shown herein, the formula should be understood also to include the linear form thereof wherein the bridge between the sulfhydryl groups of the Cys residues is not present and is replaced by hydrogen, for oxidation within the body will thereafter take place in a large number of instances.

The peptides can be synthesized by any suitable method, such as by exclusively solid-phase techniques, by partial solid-phase techniques, by fragment condensation or by classical solution addition. Synthetic CGRP and its homolog may also be synthesized by recently developed recombinant DNA techniques which may likely be used for large-scale production.

Common to coupling-type chemical syntheses of peptides is the protection of the labile side chain groups of the various amino acid moieties with suitable protecting groups which prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Also considered to be within the scope of the present invention are intermediates of the formula (II): $X^1$-Ser($X^4$)-Cys($X^2$)-Asn($X^3$)-Thr($X^4$)-Ala-Thr($X^4$)-Cys($X^2$)-Val-Thr($X^4$)-His($X^5$)-Arg($X^6$)-Leu-Ala-Gly-Leu-Leu-Ser($X^4$)-Arg($X^6$)-Ser($X^4$)-Gly-Gly-Val-Val-Lys($X^7$)-Asp($X^8$)-Asn($X^3$)-Phe-Val-Pro-Thr($X^4$)-Asn($X^3$)-Val-Gly-Ser($X^4$)-$R_{35}$($X^7$ or $X^8$)-Ala-Phe-$X^9$ wherein: the R-groups are as hereinbefore defined;

$X^1$ is either hydrogen or an α-amino protecting group. The α-amino protecting groups contemplated by $X^1$ are those known to be useful in the art in the stepwise synthesis of polypeptides. Among the classes of the α-amino protecting groups which may be used as $X^1$ are: (1) aromatic urethan-type protecting groups, such as fluorenylmethyloxycarbonyl(FMOC), benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (2) aliphatic urethan protecting groups, such as t-butyloxycarbonyl(BOC), diisopropylmethoxycarbonyl, isopropyloxycarbonyl, ethoxycarbonyl, allyloxycarbonyl; and (3) cycloalkyl urethan-type protecting groups, such as and cyclopentyloxycarbonyl, adamantyloxycarbonyl, and cyclohexyloxycarbonyl. The preferred α-amino protecting group is BOC.

$X^2$ is a protecting group for the sulfhydryl group of Cys, such as benzyl(Bzl), substituted Bzl, e.g. 3,4-dimethyl benzyl, p-methoxybenzyl(MeOBzl), p-chlorobenzyl and p-nitrobenzyl, trityl, Z, substituted Z, thioethyl, acetamidomethyl(Acm) and Bz. Acm is preferred $X^3$ is hydrogen or a protecting group for the amido group of Asn and is preferably xanthyl(Xan).

$X^4$ is a protecting group for the hydroxyl group of Thr and Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl(DCB). The most preferred protecting group is Bzl. $X^4$ can be hydrogen, which means there is no protecting group on the hydroxyl group.

$X^5$ is hydrogen or a protecting group for the imidazole nitrogen of His, such as Tos or 2,4-dinitrophenyl(DNP).

$X^6$ is a protecting group for the guanidino group of Arg preferably selected from the class consisting of nitro, p-toluenesulfonyl(Tos), Z, adamantyloxycarbonyl and BOC, or is hydrogen. Tos is most preferred.

$X^7$ is hydrogen or a protecting group for the α-amino group of Lys. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore.

$X^8$ is hydrogen or an ester-forming protecting group for the β- or γ-carboxyl group of Asp or Glu, preferably selected from the class consisting of benzyl, 2,6-dichlorobenzyl, methyll, ethyl and t-butyl ester. OBzl is most preferred.

The selection of a side chain amino protecting group is not critical except that it should be one which is not removed during deprotection of the α-amino groups during the synthesis. Hence, the α-amino protecting group and the side chain amino protecting group cannot be the same.

$X^9$ may be $NH_2$, OH, $OCH_3$, hydrazide, an ester or an ester or amide anchoring bond used in solid phase synthesis for linking to a solid resin support, represented by the formula: —O—-$CH_2$-polystyrene resin support, —O—$CH_2$-benzyl-polyamide resin support, —NH-benzhydrylamine (BHA) resin support, and —NH-paramethylbenzhydrylamine (MBHA) resin support.

The polyamide polymer is commercially available and is discussed in detail in *Bioorganic Chemistry*, 8, 351–370 (1979) where a preferred version of it is discussed in FIG. 6 therein. Use of BHA or MBHA resin is preferred, and cleavage directly gives the CGRP amide or CGRP homolog amide.

In the Formula (II) for the intermediate, at least one of $X^1$, $X^2$, $X^3$, $X^4$, $X^5$, $X^6$, $X^7$, $X^8$ and $X^9$ is a protecting group or an anchoring bond. Thus, the invention also provides a method for manufacturing a peptide having Formula (I) by (a) first forming a peptide of Formula (II) wherein: $X, X^1, X^2, X^3, X^4, X^5, X^6, X^7$, and $X^8$, are each either hydrogen or a protective group and $X^9$ is either a protective group or an anchoring bond to resin support or $NH_2$, with at least one X-group being either a protecting group or an anchoring bond; (b) splitting off the protective group or groups or anchoring bond from said peptide of Formula (II); and (c) if desired, converting a resulting peptide into a nontoxic salt thereof.

In selecting a particular side chain protecting group to be used in the synthesis of the peptides, the following rules are followed: (a) the protecting group should be stable to the reagent and under the reaction conditions selected for removing the α-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

When the peptides are not prepared using recombinant DNA technology, they are preferably prepared using solid phase synthesis, such as that described by Merrifield, *J. Am. Chem. Soc.*, 85, p. 2149 (1964), although other equivalent chemical syntheses known in the art can also be used as previously mentioned. Solid-phase synthesis is commenced from the C-terminal end of the peptide by coupling a protected α-amino acid to a suitable resin as generally set forth in U.S. Pat. No. 4,244,946 issued Jan. 21, 1981 to Rivier et al., the disclosure of which is incorporated herein by reference. Such a starting material for CGRP can be prepared by attaching α-amino-protected Phe to a BHA resin.

Phe protected by BOC is coupled to the BHA resin using methylene chloride or dimethylformamide (DMF) as solvent with a suitable coupling reagent. The selection of an appropriate coupling reagent is within the skill of the art. Particularly suitable as a coupling reagent is N,N'-dicyclohexyl carbodiimide (DCCI). The activating reagents used in the solid phase synthesis of the peptides are well known in the peptide art. Examples of suitable activating reagents are carbodiimides, such as N,N'-diisopropyl carbodiimide and N-ethyl-N'-(3-dimethylaminopropyl)carbodiimide. Other activating reagents and their use in peptide coupling are described by Schroder & Lubke, supra, in Chapter III and by Kapoor, *J. Phar. Sci.*, 59, pp 1–27 (1970).

Following the coupling of BOC-Phe to the resin support, the α-amino protecting group is removed, as by using trifluoroacetic acid(TFA) in methylene chloride, TFA alone or with HCl in dioxane. Preferably 50 weight % TFA in methylene chloride is used with 0–5 weight % 1,2 ethanedithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72–75 (Academic Press 1965).

After removal of the α-amino protecting group, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp. 1927–1938.

After the desired amino acid sequence has been completed, the intermediate peptide is removed from the resin support by treatment with a reagent, such as liquid hydrogen fluoride, which not only cleaves the peptide from the resin but also cleaves the α-amino protecting group $X^1$ and all remaining side chain protecting groups $X^3, X^4, X^5, X^6, X^7$ and $X^8$, except $X^2$ when Acm is employed, to obtain the peptide with its Cys residues still protected. The cyclic form of the peptide is obtained by oxidatively removing the protecting acetoamido-methyl groups using an iodine solution, preferably as described by Kamber, et al., *Helv. Chem. Acta.*, 63, 899 (1980). Alternatively MeOBzl may be used to protect Cys, and oxidation may be carried out using potassium ferricyanide, as described by Rivier et al., *Biopolymers*, Vol. 17 (1978), 1927–38, or by air oxidation, or in accordance with other known procedures.

The following Example sets forth the preferred method for synthesizing homologs of CGRP by the solid-phase technique.

EXAMPLE I

The synthesis of the CGRP having the formula:

H—Ser—Cys—Asn—Thr—Ala—Thr—Cys—Val—Thr—His—Arg—Leu—Ala—Gly—
Leu—Leu—Ser—Arg—Ser—Gly—Gly—Val—Val—Lys—Asp—Asn—Phe—Val—
Pro—Thr—Asn—Val—Gly—Ser—Glu—Ala—Phe—NH$_2$ is conducted in a stepwise manner on a benzhydrylamine hydrochloride resin, such as available from Bachem, Inc., having a substitution range of about 0.1 to 0.5 mmoles/gm. resin. The synthesis is performed on an automatic Beckman 990B peptide synthesizer. Coupling of BOC-Phe results in the substitution of about 0.35 mmol. Phe per gram of resin. All solvents that are used are carefully degassed, preferably by sparging with an inert gas, e.g. helium or nitrogen. The program used is generally that reported in Rivier, *J. J. Liquid Chromatogr.*, 1, 343–367 (1978).

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Arg(Tos) is being coupled, a mixture of 50% DMF and methylene chloride is used. Bzl is used as the hydroxyl side-chain protecting group for Ser and Thr. Acm is used to protect the sulfhydryl group of Cys. P-nitrophenyl ester(ONp) is used to activate the carboxyl end of Asn, and for example, BOC-Asn(ONp) is coupled overnight using one equivalent of HOBt in a 50% mixture of DMF and methylene chloride. The amido group of Asn is protected by Xan when DCCI coupling is used instead of the active ester method. 2-Cl-Z is used as the protecting group for the Lys side chain. Tos is used to protect the guanidino group of Arg and the imidazole group of His, and the side chain carboxyl group of Glu or Asp is protected by OBzl. At the end of the synthesis, the following composition is obtained BOC-Ser(Bzl)-Cys(Acm)-Asn(Xan)-Thr(Bzl)-Ala-Thr(Bzl)-Cys(Acm)-Val-Thr(Bzl)-His(tos)-Arg(tos)-Leu-Ala-Gly-Leu-Leu-Ser(Bzl)-Arg(tos)-Ser(Bzl)-Gly-Gly-Val-Val-Lys(2-Cl-Z)-Asp(OBzl)-Asn(Xan)-Phe-Val-Pro-Thr(Bzl)-Asn(Xan)-Val-Gly-Ser(Bzl)-Glu(OBzl)-Ala-Phe-resin support. Xan may have been partially or totally removed by TFA treatment used to deblock the α-amino protecting group.

In order to cleave and substantially deprotect the resulting protected peptide-resin, it is treated with 1.5 ml. anisole, 0.5 ml. of methylethylsulfide and 15 ml. hydrogen fluoride(HF) per gram of peptide-resin, first at −20° C. for 20 min. and then at 0° C. for one-half hour. After elimination of the HF under high vacuum, the resin-peptide is washed alternately with dry diethyl ether and chloroform, and the peptides are then extracted with de-gassed 2N aqueous acetic acid and separated from the resin by filtration.

The cleaved peptide is then purified by HPLC and treated with an iodide solution to deprotect the Cys residues and form the disulfide bond between the Cys residues. After cyclization, the peptide is rechromatographed for final purification using semi-preparative HPLC as described in Rivier et al., *Peptides: Structure and Biological Function* (1979) pp. 125–128. The chromatographic fractions are carefully monitored by HPLC, and only the fractions showing substantial purity were pooled.

Specific optical rotation of the CGRP peptide, which was synthesized and purified in the foregoing manner, were measured on a Perkin Elmer Model 141 as $[\alpha]_D^{20°} = -69.9° \pm 1$ (c=0.9 in 1% acetic acid) and had a purity of about 95% or greater. To check whether the precise sequence was achieved, the CGRP peptide was hydrolyzed in sealed evacuated tubes containing 4N methanesulfonic acid and 0.2% tryptamine for 24 hours at 110° C. Amino acid analysis of the hydrolysate using a Beckman 121 MB amino acid analyzer showed the predicted amino acid ratios which confirmed that the 37-residue peptide structure had been obtained.

The synthetic CGRP was examined for its effect on mean arterial blood pressure(MAP) gastric acid secretion and plasma catecholamine levels. The effects of CGRP on MAP, gastric secretion and plasma catecholamine levels were determined in unanesthetized rats and Beagle dogs. MAP was measured via direct arterial monitoring and gastric acids were collected from chronic gastric-abdominal wall cannula. Intravenous (iv) but not intercerebroventricular (icv) administration of CGRP to rats and dogs evokes a rapid decrease in MAP, and the degree and duration of hypotension are dose-related. Mean arterial blood pressure in rats fell from 106 to 57±2 mm Hg within about 1 minute following an injection of 6.5 nmoles CGRP and then slowly returned to control values during a period of more than one hour. The iv administration of an injection equal to 650 pmoles of CGRP lowered MAP to 73±3 mm Hg in about one minute, returning to control value in about 1 hour. IV and ICV administration of CGRP (10 pmoles) to rats and dogs lowers pentagastrin-induced acid secretion by more than 70% for several hours. IV and ICV administration of CGRP (6.5 nmoles) results in significant elevation of norepinephrine in plasma.

EXAMPLE II

The peptide [Lys$^{35}$]-CGRP having the formula:

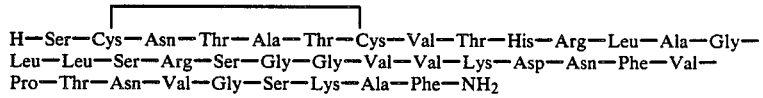

is synthesized. Testing in accordance with the general procedure set forth in Example I shows that it likewise causes a very significant lowering of MAP.

It is of interest that CGRP and its homolog exhibit such a prompt and extreme lowering of blood pressure. As a result, these peptides may be particularly valuable for the treatment of high blood pressure conditions and also for the treatment of patients who are to undergo certain types of surgery.

High quantities of CGRP are found in the trigeminal ganglion, the facial nerve and the hypoglossal nerve. These receive sensory information from the face and head as well as ennervate the salivary glands, tongue and muscles associated with chewing and swallowing. CGRP is also found in the taste buds. Therefore, CGRP and its homolog are considered useful in regulating ingestion behavior and gustatory responses and in treating patients having taste and/or sensory perception difficulties. CGRP and its homolog are also considered to be useful to desirably affect mineral and bone metabolism.

Most other regulatory peptides have been found to have effects both upon the central nervous system and upon the gastrointestinal tract. Because of its widespread distribution throughout the central nervous system, peripheral nervous system (including the autonomic nervous system) and other cells in particular tissues, including the adrenals, pancreas and gastrointestinal tract, it is likely that CGRP may subserve multiple physiological functions. CGRP and its homolog may be useful in the treatment of disorders of gastric acid secretion, such as gastric or duodenal ulcer disease. CGRP and its homolog may also find application in modifying the mood and behavior of normal and mentally disordered individuals. Because CGRP is found in both neural and nonneural tissue, administration of it or its homolog may be used to induce specific effects on the brain and its periphery, thereby influencing memory, mood, pain appreciation, etc., and more specifically, alertness, depression and/or anxiety. Particularly, such administration may be used to enhance memory and alertness, and thereby improve learning, and also to combat depression and alleviate anxiety.

CGRP or its homolog or a nontoxic addition salt thereof, combined with a pharmaceutically acceptable carrier to form a pharmaceutical composition, may be administered to mammals, including humans, either intravenously, subcutaneously, intramuscularly, percutaneously, e.g. intranasally, intracerebrospinally or orally. The peptides should be at least about 90% pure and preferably should have a purity of at least about 98% when administered to humans. However, a purity of as low as about 5% would be substantially greater than the purity of the naturally occurring compound and is considered to have utility in effecting biological responses. This purity means that the intended peptide constitutes the stated weight % of all like peptides and peptide fragments present. Their administration may be employed by a physician to lower blood pressure or to create hypotension. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. Usually, the dosage will be from about 1 to about 200 micrograms of the peptide per kilogram of the body weight of the host. As used herein all temperatures are °C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at specific positions in the CGRP peptide chain can be made in accordance with present or future developments without substantially detracting from potency and such peptides are considered as being within the scope of the invention. By consisting essentially of, for purposes of this application, is meant that the peptide is present in substantially greater purity than it is found in any natural extract and that the composition is free from any biologically active substances that would detract from its effectiveness. Fragments of these peptides which also display substantially similar biological effectiveness may also be used and are considered to be equivalents of the claimed compounds.

Various features of the invention are emphasized in the claims which follow.

What is claimed is:

1. A substantially pure synthetic peptide, or a nontoxic addition salt of a synthetic peptide, having the formula:

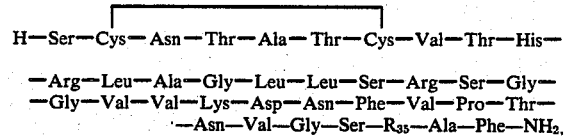

H—Ser—Cys—Asn—Thr—Ala—Thr—Cys—Val—Thr—His—

—Arg—Leu—Ala—Gly—Leu—Leu—Ser—Arg—Ser—Gly—
—Gly—Val—Val—Lys—Asp—Asn—Phe—Val—Pro—Thr—
—Asn—Val—Gly—Ser—R$_{35}$—Ala—Phe—NH$_2$.

wherein R$_{35}$ is Glu or Lys.

2. The peptide of claim 1 wherein R$_{35}$ is Glu.
3. The peptide of claim 1 wherein R$_{35}$ is Lys.
4. A pharmaceutical composition for lowering blood pressure or gastric acid secretion in mammals comprising an effective amount of a substantially pure peptide, or a nontoxic addition salt thereof, having the formula:

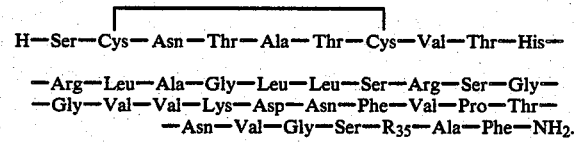

H—Ser—Cys—Asn—Thr—Ala—Thr—Cys—Val—Thr—His—

—Arg—Leu—Ala—Gly—Leu—Leu—Ser—Arg—Ser—Gly—
—Gly—Val—Val—Lys—Asp—Asn—Phe—Val—Pro—Thr—
—Asn—Val—Gly—Ser—R$_{35}$—Ala—Phe—NH$_2$.

wherein R$_{35}$ is Glu or Lys; and a pharmaceutically acceptable liquid or solid carrier therefor.

5. The composition of claim 4 wherein R$_{35}$ is Glu.
6. The composition of claim 4 wherein R$_{35}$ is Lys.
7. A method for lowering the blood pressure or gastric acid secretion of a mammal, which method comprises administering to said mammal an effective amount of a substantially pure peptide, or a nontoxic addition salt thereof, having the formula:

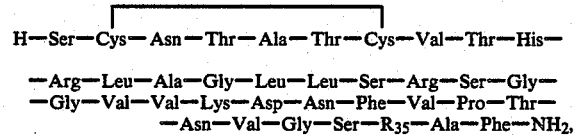

H—Ser—Cys—Asn—Thr—Ala—Thr—Cys—Val—Thr—His—

—Arg—Leu—Ala—Gly—Leu—Leu—Ser—Arg—Ser—Gly—
—Gly—Val—Val—Lys—Asp—Asn—Phe—Val—Pro—Thr—
—Asn—Val—Gly—Ser—R$_{35}$—Ala—Phe—NH$_2$, wherein R$_{35}$ is Gly or Lys.

8. The method in accordance with claim 7 wherein said administering is carried out either orally, intravenously, subcutaneously, percutaneously, intracerebrospinally or intramuscularly.
9. The method of claim 7 wherein said administration is at a level of between about 1 and about 200 micrograms per Kg. of body weight.
10. The method of claim 7 wherein R$_{35}$ is Glu.
11. The method of claim 7 wherein R$_{35}$ is Lys.

* * * * *

UNITED STATES PATENT AND TRADEMARK OFFICE
CERTIFICATE OF CORRECTION

PATENT NO. : 4,530,838
DATED : July 23, 1985
INVENTOR(S) : Evans et al.

It is certified that error appears in the above-identified patent and that said Letters Patent is hereby corrected as shown below:

Column 4, Line 35, change "a-amino" to --ε-amino--.

Column 4, Line 44, correct the spelling of --methyl--.

Claim 7, Column 10, Line 54, change "Gly" to --Glu--.

Signed and Sealed this

Thirty-first Day of December 1985

[SEAL]

Attest:

DONALD J. QUIGG

Attesting Officer

Commissioner of Patents and Trademarks